United States Patent

Gil Quintero et al.

[11] Patent Number: 5,834,493
[45] Date of Patent: Nov. 10, 1998

[54] INDOLE DERIVATIVES AS 5-HT1A AND/OR 5-HT2 LIGANDS

[76] Inventors: Myrna Gil Quintero, Via Sirte 11, 20146 Milano; Vincenzo Martino, Via Castiglioni, 5, 21056 Induno Olona (Varese); Franco Borsini, Via G. Bruno, 70, 50047 Prato (Firenze); Carlo Maria Pellegrini, Via Cappuccini, 5, 20071 Casalpusterlengo (Milan); Marco Turconi, Via Gramsci, 20, 27058 Voghera (Pavia); Ettore Giraldo, Via Monte Velino, 5, 20137 Milano, all of Italy

[21] Appl. No.: 530,354

[22] PCT Filed: Mar. 31, 1994

[86] PCT No.: PCT/EP94/01016

§ 371 Date: Dec. 1, 1995

§ 102(e) Date: Dec. 1, 1995

[87] PCT Pub. No.: WO94/24125

PCT Pub. Date: Oct. 27, 1994

[30] Foreign Application Priority Data

Apr. 8, 1993 [IT] Italy .................. MI93 A 000699

[51] Int. Cl.$^6$ .................. A16K 31/44; C07D 401/06
[52] U.S. Cl. .................. 514/339; 546/277.4
[58] Field of Search .................. 546/277.4; 514/339

[56] References Cited

FOREIGN PATENT DOCUMENTS 0429341  5/1991  European Pat. Off. .
9206973  4/1992  WIPO .

OTHER PUBLICATIONS

Malleron et al. J. Med> Chem. 36,, 1194–1202, 1993.
Smallheer et al. CA 119: 130901, 1993.
Salas et al. CA 113:78791, 1991.
Martinez et al. CA 102:78668, 1985.
J. Perregaard et al., "Selective, Centrally Acting Serotonin 5–HT$_2$Antagonists. 1.2–and 6–Substituted 1–Phenyl–3–(4–piperidinyl)–1H–indoles", *J. Med. Chem.*, 35, 4813–4822 (1992).
A. Agarwal et al., "Three Dimensional Quantitative Structure–Activity Relationships of 5–HT Receptor Binding Data for Tetrahydropyridinylindole Derivatives: A Comparison of the Hansch and CoMFA Methods", *J. Med. Chem.*, 36, 4006–4014 (1993).
E. Friderichs et al., "Darstellung der isomeren 3–(Pyridylmethyl) –und 3–(Piperidylmethyl)–5–hydroxyindole", *Archiv der Pharmazie.*308, 209–217 (1975).

*Primary Examiner*—Jane Fan
*Attorney, Agent, or Firm*—Sprung Kramer Schaefer & Briscoe

[57] ABSTRACT

Pharmacologically active indole derivatives having central serotonergic activity and useful in the treatment of CNS disorders of formula (I) wherein R, R1 and R2 have the meanings in the specification.

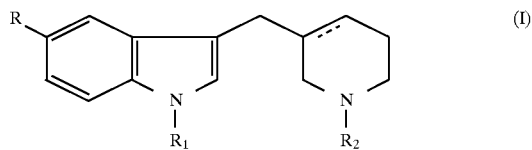

5 Claims, No Drawings

INDOLE DERIVATIVES AS 5-HT1A AND/OR 5-HT2 LIGANDS

This is a B71 of PCT/EP94/0106 filed Mar. 31, 1994 now WO 94/24125.

The present invention relates to novel pharmacologically active indole derivatives and acid addition salts thereof, to processes for their preparation and to pharmaceutical compositions containing them. The new compounds possess central serotonergic activity and are useful in the treatment of central nervous system (CNS) disorders.

It is known that 1A and 2 serotonergic receptors ($5-HT_{1A}$ and $5-HT_2$) seem to be important for many functions in the animal body. For instance, altered function of these receptors is involved in the genesis and/or treatment of anxiety, depression, psychoses, abnormality of sleep and feeding, organic mental diseases and alteration of blood pressure. In spite of the clear involvement of $5-HT_{1A}$ receptors in such a huge amount of pathological events, it is not clear why, for example, some compounds acting upon $5-HT_{1A}$ receptors exert in humans a preferential anxiolytic effects, while others exert a preferential hypotensive action. The same holds for $5-HT_2$ antagonists. This is probably due to heterogeneous characteristics, so far unknown, of $5-HT_{1A}$ and $5-HT_2$ receptors. Therefore, there is the possibility that compounds acting on $5-HT_{1A}$ and/or $5-HT_2$ receptors may exert a wide range of therapeutic effects in humans.

WO Patent 9206973 refers to 5-substituted 3(N-methyl-pyrrolidin-2-yl-methyl) indoles. The compounds are said to be useful for the treatment of depression, anxiety, migraine. WO Patent 9213856 refer to 5-heteroyl indoles. The compounds are said to be useful in treating migraine.

European Patent Application Number 429341 refer to 5-substituted to heterocyclic derivatives, including among the others, the compound named 3[N(isothiazole-dioxyde-ethyl)-1,2,3,6-tetrahydropyridin-4-ylmethyl]-indole. Such compounds are said to be 5-HT reuptake inhibitors, useful in the treatment of depression.

We have now synthetized, and this is the object of the present invention, a novel class of structurally distinct compounds showing affinity for the $5-HT_{1A}$ and/or $5-HT_2$ receptors. These new compounds may be useful in the treatment of CNS diseases such as affective disorders, (for example depression and bipolar disorders), anxiety, sleep and sexual disorders, psychosis, schizophrenia, personality disorders, mental organic disorders and mental disorders in childhood, aggressiveness, age associated memory impairment, cerebral ictus, motion sickness. Moreover they may be used for cardiovascular disorders such as hypertension and thrombosis.

The present invention has for object compounds of general formula (I)

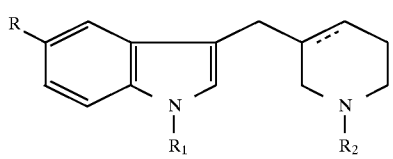

wherein:

R represents H, $C_{1-6}$ alkyl, lower alkoxy, aralkoxy, halogen, hydroxy, cyano or $C_{1-6}$ acyl;

$R_1$ represents H, $C_{1-6}$ alkyl, optionally substituted aryl, $C_{3-6}$ cycloalkyl $C_{1-2}$ alkyl or lower alkyl bearing an optionally substituted phenyl;

$R_2$ represents H, $C_{1-6}$ alkyl, lower alkyl bearing a phenyl, phenoxy or anilino, each group being optionally substituted by one or more substituents selected from lower alkyl, lower alkoxy, amino, halogen or trifluoromethyl; or $R_2$ is a group selected from

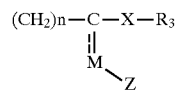 (a)

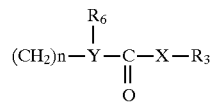 (b)

where n is an integer from 1 to 3;

$R_3$ represents an aryl or heteroaryl group, each group being optionally substituted by one or more substituents selected from lower alkyl, halogen or trifluoromethyl; $C_{1-6}$ alkyl or $C_4$–$C_{10}$ cycloalkyl;

M represents oxygen or nitrogen, or when the bond C—M is single, represents NH;

Z is absent when M is oxygen or it represents H, $C_{1-6}$ acyl or $OR_4$ where $R_4$ is hydrogen, lower alkyl, lower alkyl bearing a phenyl being optionally substituted by one or more substituents selected from lower alkyl, lower alkoxy, halogen, trifluoromethyl;

X is absent or it represents $CH_2$ or $NR_5$ where $R_5$ is H or lower alkyl;

Y represents CH or nitrogen atom;

$R_6$ represents hydrogen, lower alkyl, aryl or $R_3$ and $R_6$ together with the carbonyl group to which they are bound constitute benzocondensed cycloalkanones of formula

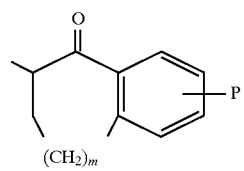 (c)

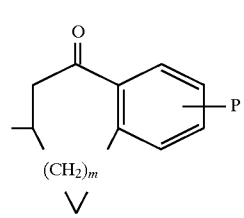 (d)

m is an integer from 0 to 2;

P represents H, lower alkyl, halogen or trifluoromethyl; and acid addition salts thereof.

For pharmaceutical use the compounds of general formula (I) may be used as such or in the form of tautomers or of physiologically acceptable acid addition salts thereof. The term "acid addition salts" includes salts either with inorganic or organic acids. Physiologically acceptable organic acids which may be used in salt formation include, for example, maleic, citric, tartaric, fumaric, methanesulphonic, acetic, benzoic, succinic, gluconic, isethionic, glycinic, lactic, malic, mucoic, glutamic, sulphamic and ascorbic acid; suitable inorganic acids include hydrochloric, hydrobromic, nitric, sulfuric or phosphoric acid.

Some of the compounds of formula (I) according to the present invention contain chiral or prochiral centres and thus may exist in different stereoisomeric forms including enantiomers of (+) and (−) type or mixtures of them. The present invention includes in its scope both the individual isomers and the mixtures thereof.

It has to be understood that, when mixtures of optical isomers are present, they may be separated according to the classic resolution methods based on their physico-chemical properties, e.g. by fractional crystallization of their acid addition salts with a suitable optically active acid or by the chromatographic separation with a suitable mixture of solvents.

In the present specification, the term $C_{1-6}$ alkyl denotes a straight or branched chain. Typical groups of that kind include methyl, ethyl, n-propyl, i-propyl, n-butyl, n-hexyl, 2-methyl-pentyl and the like. The term lower alkyl group denotes a straight alkyl group having 1 to 3 carbon atoms such as methyl, ethyl, propyl. The term lower alkoxy refers to a straight alkoxy group containing 1 to 3 carbon atoms such as methoxy, ethoxy, propoxy. The term halogen means fluorine, chlorine, bromine and iodine. Preferred halogens are fluorine, chlorine and bromine.

When R represents an aralkoxy group, it may, for example, be benzyloxy.

When $R_1$ represents a $C_{3-6}$ cycloalkyl $C_{1-2}$ alkyl group, it may, for example, be a cyclopropylmethyl, cyclopentylmethyl.

When R represents a $C_{1-6}$ acyl group, it may, for example, be a acetyl, propionyl, butyryl, pentoyl, hexoyl.

When $R_1$ is a lower alkyl bearing an optionally substituted phenyl, it may, for example, be benzyl.

When $R_1$ is optionally substituted aryl, it may, for example, be phenyl, fluorophenyl.

When $R_3$ and $R_6$ together with the carbonyl group to which they are bound form benzocondensed cycloalkanones (formula c, d) they may, for example, be indalones, tetralones.

When $R_3$ is aryl, it may, for example, be phenyl, mono-or difluorophenyl, trifluoromethylphenyl. When $R_3$ is heteroaryl, it may, for example, be thienyl. When $R_3$ is a $C_{4-10}$ cycloalkyl, it may, for example, be an adamantyl group.

The compounds of formula I wherein $R_1$ is hydrogen may be prepared by reacting compounds of the formula (II)

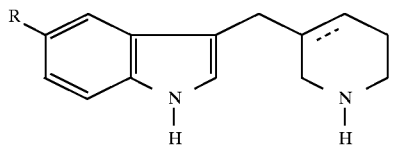

wherein R is defined above, with a compound of formula (III)

 III wherein $R_2$ is as defined above and X is a halogen atom in the presence of a base such as sodium carbonate or potassium carbonate. The reaction is carried out in an inert polar solvent such as diethyl ether, tetrahydrofuran or dimethylformamide, preferably dimethylformamide at a temperature ranging from 50° to 80° C.

The compounds of formula III are either commercially available or may be conveniently prepared by conventional methods.

The compounds of formula II, used as starting material in the above described process, may be prepared from compounds of formula IV

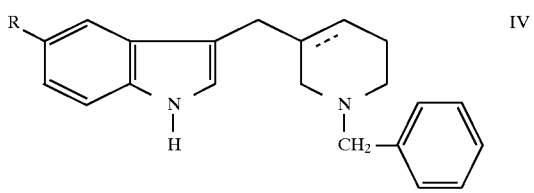

wherein R is as defined before, by debenzylation with ethyl chloroformate, followed by hydrolysis of the intermediate carbamate of formula (V)

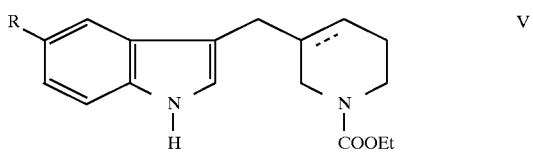

The carbamate formation is carried out in an inert solvent such as benzene or toluene, preferably toluene, at a temperature ranging from about 20° C. to about 80° C. The subsequent hydrolysis of the carbamate of formula V is carried out in basic conditions. Suitable bases are inorganic base preferably potassium hydroxide. A polar solvent should be used such as an alcohol, preferably ethanol, at a temperature of about 80° C.

The compounds of formula IV may be, in turn, prepared by hydride reduction of the quaternized salts of formula VI

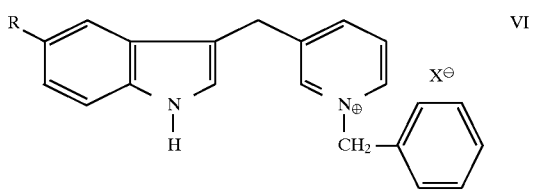

wherein R is as defined above and X is a halogen atom. Suitable hydride reducing agents include, lithium borohydride and sodium borohydride, preferably sodium borohydride. The reaction is carried out in the presence of a polar solvent such as an alcohol like ethanol, isopropanol or methanol, preferably methanol, at a temperature ranging from about −10° C. to about 10° C.

The quaternized salts of formula VI may be formed, in turn, by quaternarization of compounds of formula VII

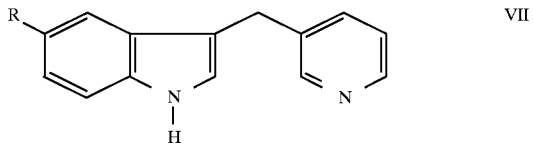

wherein R is as defined above, with a benzyl halide in the presence of suitable solvents such as ketones, for example methyl-ethyl-ketone, dimethyl-ketone preferably methyl-ethyl-ketone at a temperature ranging from 60° C. to about 90° C., preferably the reflux temperature of the solvent.

The compounds of formula VII may be, in turn, prepared by reacting a magnesium salt of an indole derivative of the formula VIII

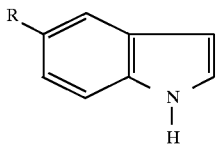

wherein R is as defined above, with the 3-chloromethylpyridine. The indole magnesium salt is first prepared from the reaction of the indole of formula VIII with an alkyl or aryl magnesium halide preferably ethylmagnesium bromide. [De Gran J. I. et al., J. Heterocyclic Chem., 3, 67 (1966)]. The reaction is generally conducted in an inert solvent at a temperature between about −30° C. and 65° C., preferably at about 25° C.

Suitable solvents include diethyl ether, tetrahydrofuran, and other alkyl ethers, preferably diethyl ether.

Preferably, a solution of the commercial 3-chloromethylpyridine in an inert solvent (e.g. diethyl ether, tetrahydrofuran or toluene) is added slowly to the solution of the magnesium salt of an indole of formula VIII at a temperature ranging from about 0° C. to about 50° C., preferably at about 25° C.

The compounds of formula VII may be, in turn, also prepared by the typical Fischer indole synthesis between an apropriate phenyl hydrazine of formula IX

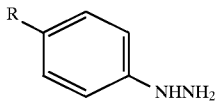

wherein R is as defined above, and the 3-pyridinpropionaldehyde. The Fischer reaction is usually carried out under acidic conditions in a polar solvent. Suitable acids for the use in the reaction include acetic acid, hydrobromic acid or hydrochloric acid, preferably hydrochloric acid. A suitable polar solvent may be an alcohol, preferably ethanol. The reaction is performed at a temperature between 60° C. and about 90° C., preferably the reflux temperature of the solvent. The 3-pyridinpropionaldehyde is prepared according to a conventional oxidation of the relative alcohol. [D. Swern et al., Tetrahedron, 34, 1651 (1978)].

The compounds of formula I, wherein $R_1$ is any meaning as defined above except hydrogen may be prepared by reacting compounds of formula I, wherein $R_1$=H, with a base such as sodium hydride, potassium hydroxide, potassium terbutylate, preferably sodium hydride. This is followed by the addition of compounds of the formula X

 $R_1$-X      X wherein $R_1$ is any meaning as defined above except hydrogen and X is halogen atom, in a stoichiometric amount. The reaction is carried out in an inert polar solvent such as diethyl ether, tetrahydrofuran or dimethylformamide, preferably dimethylformamide, at a temperature ranging from 0° to room temperature.

The compounds of formula I, wherein $R_1$ is hydrogen, may also be prepared by hydride reduction of the quaternized salts of formula

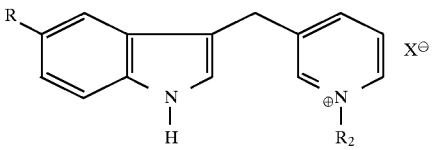

wherein R and $R_2$ are as defined above, and X is a halogen atom. Suitable hydride reducing agents include lithium borohydride and sodium borohydride, preferably sodium borohydride. The reaction is carried out in the presence of a polar solvent as an alcohol like ethanol, isopropanol or methanol, preferably methanol at a temperature ranging from −10° C. to about 10° C.

When the compounds of formula I with the 3-pyridine ring completely saturated are desired, the reduction of the quaternized salts of formula XI is carried out catalytically, under hydrogen atmosphere, preferably at a pressure of about 1 atmosphere. Suitable catalysts include Raney nickel, platinum oxide, preferably platinum oxide. The reaction is carried out in the presence of a polar solvent such as an alcohol like ethanol or methanol, preferably methanol at a temperature ranging from about 0° C. to 40° C., preferably at about 25° C.

The quaternized salts of formula XI, used as starting material in the above process, may be prepared by reacting compounds of formula VI with compounds of formula III, both already defined above.

It has to be understood that compounds of general formula (I) containing an R, $R_1$, $R_2$, $R_3$, $R_4$, $R_5$ and $R_6$, group which may give rise to another R, $R_1$, $R_2$, $R_3$, $R_4$, $R_5$ and $R_6$ group, are useful novel intermediates. Some of these transformations may also occurr in the intermediates for compounds of general formula (I).

Some examples of such conversions, which obviously are not exhaustive of all possibilities, are:
1) a nitro group may be transformed into an amino group by reduction
2) an amino group may be transformed into a $C_{1-6}$ acylamino group by acylation with a suitable carboxylic acid derivative
3) an amino group may be transformed into a lower alkyl N-mono or di-substituted group by alkylation
4) an amino group may be transformed into a lower alkoxy carbonyl amino group by reaction with a suitable reactive lower alkyl carbonic acid monoester derivative
5) a carboxyl group may be transformed into a lower alkoxy carbonyl group, or into a carbamoyl group optionally lower alkyl N-mono or di-substituted by reaction of a suitable reactive carboxylic acid derivative with appropriate alkohols and amines
6) a carbamoyl group may be transformed into a cyano group by dehydration
7) a $C_{1-6}$ alkyl thio or a $C_{1-6}$ alkyl sulphinyl group may be transformed into a $C_{1-6}$ alkyl sulphinyl or a $C_{1-6}$ alkylsulphonyl group by oxidation
8) an aromatic hydrogen may be transformed into a nitro group by nitration
9) a hydrogen group may be transformed into a halogen group by halogenation
10) a product of general formula I where $R_1$ is H obtained according to the above described process, may be transformed in a product of formula I, where $R_1$ is $C_{1-6}$ alkyl, by alkylation with a suitable alkyl halide in the presence of a strong base such as sdium or potassium hydroxide, sodium or potassium hydride, potassium t-butylate in an aprotic solvent such as dimethylformamide or tetrahydrofuran at a temperature between 20° C. and 100° C. When aqueous concentrated solutions of sodium or potassium hydroxide are used, the reaction may be conveniently carried out in the presence of an unsoluble organic solvent, such as methylene chloride in the presence of phase transfer catalyst such as a suitable ammonium quaternary salt at a temperature between 20° C. and 50° C.

11) a tertiary amino group may be transformed into a quaternary ammonium derivative by reaction with a suitable alkylating agent such as methyl bromide or methyl iodide.

These transformations are well known to any expert of the branch.

The compounds of the general formula (I) prepared according to the above methods may optionally be converted by inorganic or organic acids into non-toxic, physiologically acceptable acid addition salts, for example by conventional methods such as by reacting the compounds as bases with a solution of the corresponding acid in a suitable solvent. Example of non-toxic physiologically acceptable acid addition salts are those formed with hydrochloric, nitric sulfuric, maleic, fumaric, citric, tartaric, methanesulphonic, acetic, benzoic, succinic, gluconic, lactic, glycinic, malic, mucoic, glutamic, isethionic, phosphoric, ascorbic or sulphamic acid. Particularly preferred acids are hydrochloric, maleic and fumaric acid.

Particularly preferred compounds according to the present invention are:

5-methoxy-3-(N-methyl-1,2,5,6-tetrahydro-pyridin-3-yl-methyl)-1H-indole (Compound 1)

5-methoxy-3-[N-(2-(4-amino-phenyl)-ethyl)-1,2,5,6-tetrahydro-pyridin-3-ylmethyl]-1H-indole (Compound 13)

5-methoxy-3-[N-(4'-fluoro-phenoxy-ethyl)-1,2,5,6-tetrahydro-pyridin-3-ylmethyl]-1H-indole (Compound 2)

5-methoxy-3-[N-(4-(4-fluoro-phenyl)-4-oxo-butyl)-1,2,5,6-tetrahydro-pyridin-3-ylmethyl]-1H-indole (Compound 9)

5-methoxy-3-[N-(3-(4-fluoro-phenyl)-3-oxo-propyl)-1,2,5,6-tetrahydro-pyridin-3-ylmethyl]-1H-indole (Compound 11)

5-methoxy-3-[N-(4-(4-fluoro-phenyl)-butyl)-1,2,5,6-tetrahydro-pyridin-3-ylmethyl]-1H-indole (Compound 14)

5-methoxy-3-[N-2(4-fluoro-benzamide)ethyl]- 1,2,5,6-tetrahydro-pyridin-3-ylmethyl]-1H-indole (Compound 16)

5-methoxy-3-[N-(3-(4-fluoro-phenyl)-propyl)-1,2,5,6-tetrahydro-pyridin-3-ylmethyl]-1H-indole (Compound 15)

5-methoxy-3-[N-(4-(2-thienyl)-4-oxo-butyl)-1,2,5,6-tetrahydro-pyridin-3-ylmethyl]-1H-indole (Compound 32)

As already mentioned hereinbefore, the new compounds of formula (I), according to the present invention, show interesting pharmacological properties owing to their activity on CNS serotonergic receptors, particularly 5-HT$_{1A}$ and/or 5-HT$_2$ receptor subtypes. Therefore the new compounds are commercially useful in the prevention and in the treatment of disorders wherein the altered functionality of 5-HT$_{1A}$ and/or 5-HT$_2$ receptors, as above mentioned, is involved.

The biochemical and pharmacological profile of the compounds object of the present invention was assessed by evaluating their affinity for 5-HT$_{1A}$ and 5-HT$_2$ receptors and their efficacy was established: a) in inducing the well-known behavioural syndrome due to the stimulation of 5-HT$_{1A}$ receptors and b) by evaluating the antagonism towards the behavioural syndrome induced by quipazine stimulating the 5-HT$_2$ receptors.

Receptor Binding Studies

Receptor binding studies on 5-HT$_{1A}$ and 5-HT$_2$ receptors were carried out to determine the affinity of the test compounds.

5-HT$_{1A}$ Receptors

Tissue preparation

Rats (male Sprague Dawley, 200–250 g) were used. The Hippocampi of these animals were homogeneized in 10 volumes of ice cold TRIS buffer (pH 7.4). The homogenate was diluted 1:400 (w:v) in the same buffer to have a final protein concentration of about 200 µg/mL, filtered and incubated at 37° C. for 10 min, before use.

Binding assay

Displacement experiments were performed by incubating the homogenate (980 µL) in the presence of [$^3$H]-8OH-DPAT (1.0–1.5 nM) (10 µL) and of different concentrations of the test compounds dissolved in the test buffer (10 µL), at 30° C. for 15 min (final volume: 1 mL).

Non specific binding was determined in the presence of 100 µM 5-HT (10 µL). The separation of [3H]-8-OH-DPAT, free from that bound to the receptor, was carried out by the filtration technique (GF/B filters, Whatman). The radioactivity present was counted by liquid scintillation spectrometry.

Data analysis

The affinity values (Ki) for the compounds were obtained by a non linear least squares regression analysis on the basis of a one binding site model. The values were corrected on the basis of the radioligand occupancy on the receptors according to the equation: $Ki=IC_{50}/(1+[C]/K_D)$, where [C] and $K_D$ represent the concentration and the dissociation constant, respectively, of the radioligand used ([$^3$H]-8-OH-DPAT).

5-HT$_2$ Receptors

Tissue preparation

Rats (male Sprague Dawley, 200–250 g) were used. Cerebral cortices were homogenized in 10 volumes of ice cold 0.32M sucrose. After the centrifugation of the homogenate (1,000×g for 10 min) the supernatant was then recentrifuged at 48,000×g for 15 min. The resulting pellet was resuspended in 10 volumes of 50 mM TRIS buffer (pH 7.4), incubated at 37° C. for 10 min and recentrifuged at 48,000×g for 15 min. The residue was then resuspended in 10 volumes of 50 mM TRIS buffer (pH 7.4).

Binding assay

The tissue was diluted 1:100 (w:v) in 50 mM TRIS buffer (pH 7.4) to have a final protein concentration of about 200 µg/mL.

Displacement experiments were performed by incubating the homogenate (980 µL) in the presence of [$^3$H]-Ketanserine (0.5–1.0 nM) (10 µL) and of different concentrations of the test compounds dissolved in the assay buffer (10 µL), at 37° C. for 10 min (final volume: 1 mL).

Non specific binding was determined in the presence of 100 µM Methysergide (10 µL). The separation of [$^3$]-Ketanserine free from that bound to the receptor was carried by the filtration technique (GF/B filters, Whatman). The radioactivity present was counted by liquid scintillation spectrometry.

Data analysis

The affinity values (Ki) for the compounds were obtained by non linear least squares regression analysis on the basis of a one binding site model. These values were corrected on the basis of the radioligand occupancy on the receptors according to the equation: $K_i = IC_{50}/(1+[C]/K_D)$, where [C] and $K_D$ represent the concentration and the dissociation constant, respectively, of the radioligand used ($[^3H]$-Ketanserine).

The results of some of the compounds of the present invention on the affinity to the $5\text{-}HT_{1A}$ and $5\text{-}HT_2$ receptors are reported in Tables 1 and 2.

TABLE 1

AFFINITY FOR 5-HT$_{1A}$ RECEPTORS

| Compound | Ki (nM) |
|---|---|
| 1 | 35 |
| 2 | 10 |
| 9 | 30 |
| 11 | 30 |
| 13 | 100 |
| 14 | 80 |
| 16 | 1 |
| 17 | 1 |
| 15 | 10 |
| 32 | 30 |

TABLE 2

AFFINITY FOR 5-HT$_2$ RECEPTORS

| Compound | Ki (nM) |
|---|---|
| 2 | 50 |
| 9 | 15 |
| 11 | 20 |
| 13 | 50 |
| 14 | 100 |
| 15 | 10 |
| 32 | 10 |

According to a further feature of the present invention there are provided pharmaceutical compositions comprising as active ingredient at least one compound of formula (I), as hereinbefore defined, or a physiologically acceptable acid addition salt thereof in association with one or more pharmaceutical carriers, diluents or excipients. For pharmaceutical administration the compounds of general formula (I) and their physiologically acceptable acid addition salts may be incorporated into the conventional pharmaceutical preparations in solid, liquid or spray form. The compositions may, for example, be presented in a form suitable for oral, rectal, parenteral administration or for nasal inhalation. Preferred forms include, for example, capsules, tablets, coated tablets, ampoules, suppositories and nasal spray.

The active ingredient may be incorporated in excipients or carriers conventionally used in pharmaceutical compositions such as, for example, talc, arabic gum, lactose, gelatine, magnesium stearate, corn starch, aqueous or non-aqueous vehicles, polyvinylpirrolidone, semisynthetic gliceride of fatty acids, benzalcon chloride, sodium phosphate, EDTA, polysorbate 80.

In order to increase the solubility of the compounds of general formula (1) or their physiological acceptable salts, surfactants, non-ionic surfactants such as PEG 400, cyclodextrins, metastable polymorphs, inert absorbents such as bentonite may be incorporate. Furthermore some techniques may be employed by preparing for example eutetic mixtures and/or solid dispersions by using mannitol, sorbitol, saccharose, succinic acid, or physical modified forms by using hydrosoluble polymers, PVP, PEG 4000–20000.

The compositions are advantageously formulated in dosage units, each dosage unit being adapted to supply a single dose of the active ingredient. Each dosage unit may conveniently contain from 0,01 mg to 100 mg and preferably from 0,1 mg to 50 mg.

The following examples illustrate the preparation of some new compounds according to the present invention and will enable other skilled in the art to understand it more completely. It should be understood, however, that the invention is not limited solely to the particular examples given below.

Description 1
5-methoxy-3-(pyridin-3-ylmethyl)-1H-indole

The above mentioned compound was prepared analogously to the procedure described in J. Het. Chem. 3, 67 (1966) from 5-methoxy-indolyl-magnesium bromide and 3-chloromethylpyridine. After purification by Flash Chromatography on silica gel using as eluent methylene chloride/methanol/ammonia (98:2:0,1), the desired compound was obtained.

Mp 112° C.

Analogously were prepared:

5-Fluoro-3-(pyridin-3-ylmethyl)-1H-indole
Mp 108° C.
5-methyl-3-(pyridin-3-ylmethyl)-1H-indole
Mp 110° C.

Description 2
5-benzyloxy-3-(pyridin-3-ylmethyl)-1H-indole

The above mentioned compound was prepared similarly to the procedure described in Arch. Pharm. 308, 209 (1975) from 5-benzyloxy-indolyl-magnesium bromide and 3-chloromethyl-pyridine. After recrystallization from acetonitrile, the desired compound was obtained.

Mp 148° C.

Description 3
5-bromo-3-(pyridin-3-ylmethyl)-1H-indole i) 3-Pyridin-propionaldehyde The above mentioned compound was prepared analogously to the procedure described in Tetrahedron 34, 1651 (1978).

The compound was used as such without further purification.

ii) 5-Bromo-3-(pyridin-3-ylmethyl)-1H-indole

A mixture of 3-pyridin-propionaldehyde (1 g; 0.0074 mol) and of 4-bromophenylhydrazin hydrochloride (1.8 g; 0.0074 mol) with acetic acid (4.44 ml) in absolute ethanol (50 ml) was refluxed for 3 hours. The reaction was then quenched with a saturated solution of aqueous sodium carbonate and the product was extracted with ethyl acetate. The organic extract was dried ($MGSO_4$) and evaporated under vacuum. After purification by Flash Chromatography on silica gel using as eluent methylene chloride/methanol (98/2), the desired compound was obtained.

Mp 122° C.

Following the above described process and using the appropriate substituted phenylhydrazine the following compounds were prepared:

5-chloro-3-(pyridin-3-ylmethyl)-1H-indole
Mp 125° C.
5-fluoro-3-(pyridin-3-ylmethyl)-1H-indole
Mp 109° C.
5-methoxy-3-(pyridin-3-ylmethyl)-1H-indole
Mp 112° C.

Description 4
5-Cyano-3-(pyridin-3-ylmethyl)-1H-indole

A mixture of compound of Description 3 [5-Bromo-3-(pyridin-3-ylmethyl)-1H-indole] (1.1 g; 0.0038 mol) and copper cyanide (0.86 g; 0.0096 mol) in dimethylformamide (35 ml) was treated at 140° C. for 8 hours. The reaction mixture was poured into an ice ammonium hydroxide solution and the product was extracted with ethyl acetate. The organic extract was dried (MgSO$_4$) and evaporated under vacuum. After purification by Flash Chromatography on silica gel using as eluent methylene chloride/methanol (97/3), the desired compound was obtained.

Mp 125° C.

Description 5

5-methoxy-3-(1,2,5,6-tetrahydro-pyridin-3-ylmethyl)-1H-indole i) 3[(5-methoxy-1H-indol-3-yl)methyl]-1-benzyl-pyridinium bromide Benzyl bromide (8.7 ml; 0.073 mol) was added to a stirring mixture of compound of Description 1 [5-methoxy-3-(pyridin-3-ylmethyl)-1H-indole] (3.5 g; 0.0146 mol) in methyl ethyl ketone (70 ml). The reaction mixture was refluxed for 3 hours. The product precipitated as a yellow solid was filtered and washed with diethyl ether and dried under vacuum. The compound was used as such without further purification.

ii) 5-Methoxy-3-(N-benzyl-1,2,5,6-tetrahydro-pyridin-3-ylmethyl)-1H-indole

Sodium borohydride in pellets (1.5 g; 0.0396 mol) was added to a cold (0° C.) stirring mixture of 3[(5-methoxy-1H-indol-3-yl)methyl]-1-benzyl-pyridinium bromide (5.8 g; 0,0141 mol) in methanol (130 ml). The reaction mixture was stirred at 0° C. for 2 hours. The product precipitated as a whitepink solid was filtered and washed with cold methanol and dried under vacuum.

iii) 5-Methoxy-3-(N-ethoxycarbonyl-1,2,5,6-tetrahydro-pyridin-3-ylmethyl)-1H-indole Ethyl chloroformate (5.74 ml; 0.060 mol) was added to a mixture of 5-methoxy-3-(N-benzyl-1,2,5,6-tetrahydro-pyridin-3-ylmethyl)-1H-indole (4 g; 0.012 mol) in toluene (430 ml). The reaction mixture was heated at 75° C. for 3 hours. The reaction mixture was then cooled and the desired compound was obtained after evaporation of the solvent. The compound was used as such without further purifiction.

iiii) 5-Methoxy-3-(1,2,5,6-tetrahydro-pyridin-3-ylmethyl)-1H-indole

A mixture of 5-methoxy-3-(N-ethoxycarbonyl-1,2,5,6-tetrahydro-pyridin-3-ylmethyl)-1H-indole (3.8 g; 0.012 mol) with a saturated (45%) aqueous solution of potassium hydroxide (208 ml) in absolute ethanol (313 ml) was refluxed for 12 hours. The reaction mixture was then cooled and the ethanol was evaporated under vacuum. The residual alkaline aqueous solution was diluted with water. Then the product was extracted several times with ethyl acetate. The organic extract was dried (MgSO$_4$) and evaporated under wacuum. The desired compound was obtained after trituration of the solid residue with diethyl ether.

Mp 139°–145° C.

Following the above described process and using the appropriate indole derivative already described in Description 1 and Description 3, the following compound was prepared:

5-Bromo-3-(1,2,5,6-tetrahydro-pyridin-3-ylmethyl)-1H-indole

Mp 140°–145° C.

Description 6

5-methoxy-3-(Piperidin-3-ylmethyl)-1H-indole i) 5-methoxy-3-(pyridin-3-ylmethyl)-1H-indole hydrochloride A solution of compound of Description 1 [5-methoxy-3-(pyridin-3-ylmethyl)-1H-indole] (3 g) in diethyl ether was saturated with gaseous hydrogen chloride. A solid was precipitated. The title compound was collected by filtration washed with diethyl ether and dried under vacuum. The compound was used as such without further purification.

ii) 5-methoxy-3-(piperidin-3-ylmethyl)-1H-indole

The above mentioned compound was prepared analogously to the procedure described in Arch. Pharm. 308, 209 (1975) from 5-methoxy-3-(pyridin-3-yl-methyl)-1H-indole hydrochloride.

Mp 150°–160° C.

Description 7

3-[(5-methoxy-1H-indol-3-yl)methyl]-1-methyl-pyridinium iodide

Methyl iodide (10.4 ml; 0.167 mol) was added to a stirring mixture of compound of Description 1 [5-methoxy-3-(pyridin-3-ylmethyl)-1H-indole] (5.3 g; 0.022 mol) in acetone (150 ml). The reaction mixture was stirred at room temperature for 18 hours. The reaction mixture was concentrated under vacuum. The residual solid was washed with diethyl ether giving the desired compound (7.5 g).

Following the above described process and using the appropriate halide and the appropriate indole derivative already described in Description 1 the following compounds can be prepared:

3-[(5-methoxy-1H-indol-3-yl)methyl]-1-[2-(4-nitro-phenyl)-ethyl)]-pyridinium bromide 3-[(5-methoxy-1H-indol-3-yl)methyl]-1-[(4'-fluoro-phenoxy)-ethyl)]-pyridinium bromide 3-[(5-methoxy-1H-indol-3-yl)methyl]-1-propyl-pyridinium bromide 3-[(5-bromo-1H-indol-3-yl)methyl]-1-methyl-pyridinium bromide 3-[(5-bromo-1H-indol-3-yl)methyl]-1-ethyl-pyridinium bromide 3-[(5-cyano-1H-indol-3-yl)methyl]-1-methyl-pyridinium bromide 3-[(5-cyano-1H-indol-3-yl)methyl]-1-ethyl-pyridinium bromide 3-[(5-methyl-1H-indol-3-yl)methyl]-1-ethyl-pyridinium bromide All the above mentioned compounds were used as such without further purification.

EXAMPLE 1

5-methoxy-3-(N-methyl-1,2,5,6-tetrahydro-pyridin-3-yl-methyl)-1H-indole (Compound 1)

Sodium borohydride in pellets (5.71 g; 0.0396 mol) was added to a cold (~0° C.) stirring mixture of compound of Description 7 [3-[(5-methoxy-1H-indol-3-yl)methyl]-1-methyl-pyridinium iodide] (7.45 g; 0.0196 mol) in methanol (150 ml). The reaction mixture was stirred at 0° C. for 2 hours. The reaction was then quenched with a saturated solution of aqueous sodium carbonate and the solvent (methanol) was evaporated under vacuum. The product was extracted with methylene chloride from the residual alkaline aqueous solution. The organic extract was dried (MgSO$_4$) and evaporated under vacuum. Purification by Flash Chromatography of the crude product using silica gel and elution with methylene chloride/methanol/ammonia (90/10/1) yielded the desired compound. A solution of the desired compound in diethyl ether was saturated with gaseous hydrogen chloride. A white solid was precipitated. The title compound hydrochloride was collected by filtration, washed with diethyl ether and dried under vacuum (3.5 g).

Mp 192° C.

Analysis
C₁₆H₂₀N₂·HCl

|  | C | H | N | Cl |
|---|---|---|---|---|
| Found % | 64.71 | 7.29 | 9.36 | 12.00 |
| Calc. % | 65.63 | 7.23 | 9.50 | 12.11 |

¹H NMR (DMSO+CDCl₃) δ=10.9–10.3 (b, 2H), 7.23 (d, 1H), 7.12 (d, 1H), 6.94 (d, 1H), 6.70 (m, 1H), 5.75 (b, 1H), 3.77 (s, 3H), 3.8–2.2 (8H), 2.76 (d, 3H); MS (C.I.): [M+H]⁺ 257 m/z

Following the above described process and using the appropriate pyridinium salt, the following compounds can be prepared:

5-methoxy-3-[N-(4'-fluoro-phenoxy-ethyl)-1,2,5,6-tetrahydro-pyridin-3-yl-methyl]-1H-indole (Compound 2)
Mp 60° C.

Analysis
C₂₃H₂₅FN₂O₂·HCl

|  | C | H | N |
|---|---|---|---|
| Found % | 64.96 | 6.52 | 6.65 |
| Calc. % | 66.26 | 6.29 | 6.72 |

¹H NMR (DMSO+CDCl₃) δ=12.43 (b, 1H), 8.68 (b, 1H), 7.29 (d, 1H), 7.0–6.6 (7H), 5.84 (b, 1H), 4.35 (b, 2H), 3.82 (s, 3H), 3.9–1.8 (10 H); MS (C.I.): (M+H)⁺ 381 m/z 5-methoxy-3-[N-propyl-1,2,5,6-tetrahydro-pyridin-3-yl-methyl]-1H-indole (Compound 3)
Mp 80°–85° C.

Analysis
C₁₈H₂₄N₂O

|  | C | H | N |
|---|---|---|---|
| Found % | 74.10 | 8.57 | 9.30 |
| Calc. % | 76.02 | 8.55 | 9.15 |

¹H NMR (DMSO+CDCl₃) δ=10.59 (b, 1H), 7.21 (d, 1H), 7.03 (1d, 1H), 6.95 (1d, 1H), 6.70 (dd, 1H), 5.52 (b, 1H), 3.73 (s, 3H), 3.30 (b, 2H), 2.81 (b, 2H), 2.6–1.9 (6H), 1.34 (m, 2H), 0.80 (t, 3H); MS (C.I.): [M+H]⁺ 285 m/z 5-bromo-3-[N-methyl-1,2,5,6-tetrahydro-pyridin-3yl-methyl]-1H-indole (Compound 4)
Mp 131°–133° C.

Analysis
C₁₅H₁₇N₂Br

|  | C | H | N |
|---|---|---|---|
| Found % | 58.98 | 5.64 | 9.10 |
| Calc. % | 59.03 | 5.61 | 9.18 |

¹H NMR (DMSO+CDCl₃) δ=11.19 (b, 1H), 10.81 (b, 1H), 7.64 (d, 1H), 7.35 (d, 1H), 7.26 (d, 1H), 7.13 (m, 1H), 5.72 (b, 1H), 3.6–3.2 (6H), 2.76 (s, 3H), 2.48 (b, 2H); MS (C.I.): [M+H]⁺ 306 m/z 5-bromo-3-[N-ethyl-1,2,5,6-tetrahydro-pyridin-3-yl-methyl]-1H-indole (Compound 5)
Mp 132°–134° C.

Analysis
C₁₆H₁₉N₂Br

|  | C | H | N |
|---|---|---|---|
| Found % | 59.91 | 6.04 | 8.66 |
| Calc. % | 60.20 | 6.00 | 8.77 |

¹H NMR (CDCl₃) δ=9.25 (b, 1H), 7.69 (d, 1H), 7.3–7.1 (2H), 6.90 (d, 1H), 5.56 (b, 1H), 3.35 (s, 2H), 2.92 (s, 2H), 2.58 (t, 2H), 2.49 (q, 2H), 2.24 (b, 2H), 1.08 (t, 3H); MS (C.I.): [M+H]⁺ 320 m/z 5-cyano-3-[N-methyl-1,2,5,6-tetrahydro-pyridin-3yl-methyl]-1H-indole (Compound 6)
Mp 166°–167° C.

Analysis
C₁₆H₁₇N₃

|  | C | H | N |
|---|---|---|---|
| Found % | 75.8 | 6.95 | 16.3 |
| Calc. % | 76.46 | 6.82 | 16.72 |

¹H NMR (CDCl₃) δ=9.46 (b, 1H), 7.91 (s, 1H), 7.4–7.2 (2H), 7.04 (d, 1H), 5.03 (b, 1H), 3.40 (b, 2H), 2.87 (d, 2H), 2.57 (m, 2H), 2.35 (s, 3H), 2.5–2.2 (2H); MS (C.I.): [M+H]⁺ 252 m/z 5-cyano-3-[N-ethyl-1,2,5,6-tetrahydro-pyridin-3-yl-methyl]-1H-indole (Compound 7)
Mp 105°–107° C.

Analysis
C₁₇H₁₉N₃

|  | C | H | N |
|---|---|---|---|
| Found % | 76.86 | 7.35 | 16.02 |
| Calc. % | 76.95 | 7.22 | 15.84 |

¹H NMR (CDCl₃) δ=10.10 (b, 1H), 7.93 (d, 1H), 7.5–7.3 (2H), 6.99 (d, 1H), 5.62 (b, 1H), 3.40 (s, 2H), 2.93 (s, 2H), 2.62 (t, 2H), 2.52 (q, 2H), 2.27 (b, 2H), 1.08 (t, 3H); MS (C.I.): [M+H]⁺ 266 m/z 5-methyl-3-[N-methyl-1,2,5,6-tetrahydro-pyridin-3-yl-methyl]-1H-indole (Compound 8)
Mp 96°–105° C.

Analysis
C₁₆H₂₀N₂·HCl

|  | C | H | N |
|---|---|---|---|
| Found % | 69.1 | 7.35 | 9.8 |
| Calc. % | 69.42 | 7.65 | 10.12 |

¹H NMR (CDCl₃) δ=12.56 (b, 1H), 8.29 (b, 1H), 7.3–7.2 (2H), 7.1–7.0 (2H), 5.87 (b, 1H), 3.76 (gem, 1H), 3.8–3.5

(3H), 3.13 (m, 1H), 3.0–2.7 (2H), 2.66 (d, 3H), 2.33 (m, 1H), 2.45 (s, 3H); MS (C.I.): [M+H]⁺ 241 m/z

EXAMPLE 2

5-methoxy-3-[N-(4-(4-fluoro-phenyl)-4-oxo-butyl)-1,2,5,6-tetrahydro-pyridin-3-ylmethyl]-1H-indole (Compound 9)

A mixture of compound of Description 5 [5-methoxy-3-(1,2,5,6-tetrahydro-pyridin-3-ylmethyl)-1H-indole] (1.5 g; 0.0062 mol), potassium carbonate (4.3 g; 0.031 mol), KI (0.06 g; 0.0004 mol) and 2-(3-chloropropyl)-2-(4-fluorophenyl)-1,3-dioxolane (1.3 ml; 0.0064 mol) in dry dimethylformamide (30 ml) was heated at 80° C. for 6 hours. The reaction mixture was cool down to room temperature, quenched with water and then extracted with diethyl ether. The organic extract was dried (MgSO₄) and evaporated under vacuum. The residue was taken up in a solution of hydrochloric acid (37%; 6 ml) in methanol (30 ml). The resulting mixture was stirred for 2 hours at room temperature. The reaction was then quenched with a saturated solution of aqueous sodium carbonate and the solvent (methanol) was evaporated under vacuum. The residual alkaline aqueous solution was extracted with methylene chloride. The organic extract was dried (MgSO₄) and evaporated under vacuum. After purification by Flash Chromatography on silica gel using as eluent methylene chloride/methanol/ammonia (95/5/0,5), the desired compound was obtained (1,72 g). A solution of the compound in ethanol was saturated with gaseous hydrogen chloride. A white solid was precipitated. The title compound hydrochloride was collected by filtration, washed with ethanol and dried under vacuum.

Mp 95°–97° C.

| Analysis C₂₅H₂₇FN₂O₂.HCl | | | |
|---|---|---|---|
| | C | H | N |
| Found % | 66.24 | 6.58 | 6.11 |
| Calc. % | 67.79 | 6.37 | 6.32 |

¹H NMR (DMSO+CDCl₃) δ=12.18 (b, 1H), 8.59 (s, 1H), 7.88 (m, 2H), 7.3–6.7 (6H), 5.84 (b, 1H), 3.81 (s, 3H), 4.1–1.9 (14H); MS (C.I.): [M+H]⁺ 407 m/z

Following the above described process and using the appropriate indole derivative already described in Description 5, the following compound was prepared:

5-bromo-3-[N-(4-(4-fluoro-phenyl)-4-oxo-butyl)-1,2,5,6-tetrahydro-pyridin-3-ylmethyl]-1H-indole (Compound 10) Mp 237° C.

| Analysis: C₂₄H₂₄BrFN₂O.HCl | | | |
|---|---|---|---|
| | C | H | N |
| Found % | 58.23 | 5.18 | 5.63 |
| Calc. % | 58.61 | 5.12 | 5.70 |

¹H NMR (DMSO) δ=11.25 (s, 1H), 10.64 (b, 1H), 8.06 (m, 2H), 7.69 (d, 1H), 7.4–7.3 (4H), 7.17 (m, 1H), 5.71 (b, 1H), 3.77 (gem, 1H), 3.7–3.4 (4H), 3.3–3.0 (5H), 2.7–2.4 (1H), 2.26 (gem, 1H), 2.01 (m, 2H); MS (C.I.): [M+H]⁺ 456 m/z 3-[N-(4-(4-fluoro-fenil)-4-oxo-butyl)-1,2,5,6-tetrahy-dro-pyridin-3-ylmethyl]-1H-indole (Compound 40)

EXAMPLE 3

5-methoxy-3-[N-(3-(4-fluoro-phenyl)-3-oxo-propyl)-1,2,5,6-tetrahydro-pyridin-3-ylmethyl]-1H-indole (Compound 11)

Triethylamine (0.9 ml; 0.0063 mol) was added to a solution of 3-chloro-4'-fluoropropiophenone (1.2 g; 0.0063 mol) in diethyl ether (10 ml). The resulting mixture was stirred for 3 hours at room temperature. Then the mixture was filtered and the filtrate was concentrated under vacuum. The residue was taken up with a mixture of compound of Description 5 [5-methoxy-3-(1,2,5,6-tetrahydro-pyridin-3-ylmethyl)-1H-indole] (0.79 g; 0.0028 mol), triethylamine (0.8 ml; 0.0057 mol) in methylene chloride (20 ml). The reaction mixture was refluxed for 4 hours. Then the reaction was concentrated under vacuum and the residue was triturated with 1N hydrochloric acid. The aqueous phase was decanted, and the guming solid was twice washed with water and triturated with diethyl ether. The title compound hydrochloride was collected by filtration, washed with diethyl ether and recrystallized with a mixture (½) of ethyl acetate/acetone. 0.86 g of the desired compound were obtained.

Mp 186°–188° C.

| Analysis C₂₄H₂₅FN₂O₂.HCl | | | |
|---|---|---|---|
| | C | H | N |
| Found % | 66.83 | 6.29 | 6.42 |
| Calc. % | 67.20 | 6.11 | 6.53 |

¹H NMR (DMSO+CDCl₃) δ=10.79 (b, 1H), 10.45 (b, 1H), 8.08 (m, 2H), 7.40 (m, 2H), 7.23 (d, 1H), 7.18 (d, 1H), 6.98 (d, 1H), 6.72 (m, 1H), 5.80 (b, 1H); MS (C.I.): [M+H]⁺ 393 m/z

Following the above described process and using the appropriate halide, the following compound was prepared:

5-methoxy-3-[N-(3-(2,4-difluoro-phenyl)-3-oxo-propyl)-1,2,5,6-tetrahydro-pyridin-3-ylmethyl]-1H-indole (Compound 12)
Mp 185° C.

| Analysis C₂₄H₂₄F₂N₂O₂ | | | |
|---|---|---|---|
| | C | H | N |
| Found % | 69.15 | 5.97 | 6.63 |
| Calc. % | 70.33 | 5.89 | 6.82 |

Description 8
5-methoxy-3-[N-(2-(4-nitro-phenyl)-ethyl)-1,2,5,6-tetrahydro-pyridin-3-ylmethyl]-1H-indole Sodium borohydride in pellets (0.8 g; 0.0211 mol) was added to a cold (~0° C.) stirring mixture of compound of Description 7 [3-[(5-methoxy-1H-indol-3-yl)-methyl]-1-(2-(4-nitro-phenyl)-ethyl)-pyridinium bromide] (1.75 g; 0.0038 mol) in methanol (50 ml). The reaction mixture was stirred at 0° C. for 2 hours. The reaction was then quenched with a saturated solution of aqueous sodium carbonate and the solvent (methanol) was evaporated under vacuum. The product was extracted with methylene chloride. The organic extract was dried (MgSO₄) and evaporated under vacuum giving the desired compound (1.38 g). The compound was used as such without further purification.

EXAMPLE 4

5-methoxy-3-[N-(2-(4-amino-phenyl)-ethyl)-1,2,5,6-tetrahydro-pyridin-3-ylmethyl]-1H-indole (Compound 13)

Iron powder (0.97 g; 0.0174) was added to a suspension of the compound of Description 8 [5-methoxy-3-[N-(2-(4-nitro-phenyl)-ethyl)-1,2,5,6-tetrahy-dro-pyridin-3-ylmethyl]-1H-indole] (1.36 g; 0.0035 mol) in 10% aqueous hydrochloric acid (70 ml). The reaction mixture was refluxed for 3 hours. The reaction mixture was then cool down to room temperature and quenched with a saturated solution of aqueous sodium carbonate. The resulting mixture was filtered through diatomaceous earth (Celite$^{(R)}$), washed with water and extracted with methylene chloride. The organic extract was dried ($MgSO_4$) and evaporated under vacuum. After purification by Flash Chromatography on silica gel using as eluent methylene chloride/methanol/ammonia (95/5/0.5), the title compound was obtained as a yellow solid (0.2 g).

Mp 76°–79° C.

| | Analysis $C_{23}H_{27}N_3O$ | | |
|---|---|---|---|
| | C | H | N |
| Found % | 74.53 | 7.71 | 11.31 |
| Calc. % | 76.42 | 7.53 | 11.62 |

$^1$H NMR ($CDCl_3$) δ=8.15 (b, 1H), 7.3–6.4 (6H), 6.57 (d, 2H), 5.58 (b, 1H), 3.83 (s, 3H), 3.38 (b, 4H), 3.2–2.5 (8H), 2.22 (b, 2H); MS (C.I.): [M+H]$^+$ 262 m/z

Description 9

1-(4-chloro-butyl)-4-fluoro-benzene

Triethylsilane (22.5 ml; 0.141 mol) was added dropwise to a cold (~0° C.) stirring mixture of 4-chloro-4'-fluoro-butyrophenone (10 ml; 0.0613 mol) in trifluoroacetic acid (47 ml). The reaction mixture was stirred at room temperature under nitrogen for 6 hours. The reaction was quenched with brine and extracted with diethyl ether. The organic extract was dried ($MgSO_4$) and evaporated under vacuum giving the desired compound as an oil.

Following the above described process and using the appropriate acyl halide the following compound can be prepared:

1-(3-chloro-propyl)-4-fluoro-benzene.

All the above mentioned compounds were used as such without further purification.

EXAMPLE 5

5-methoxy-3-[N-(4-(4-fluoro-phenyl)-butyl)-1,2,5,6-tetrahydro-pyridin-3-ylmethyl]-1H-indole (Compound 14)

A mixture of compound of Description 5 [5-methoxy-3-(1,2,5,6-tetrahydro-pyridin-3-ylmethyl)-1H-indole] (1.4 g; 0.0058 mol), potassium carbonate (4 g; 0.0029 mol), a catalytic amount of potassium iodide (0.030 g) and compound of Description 9 [1-(4-chloro-butyl)-4-fluoro-benzene] (5.4 g; 0.029 mol) in dimethylformamide (40 ml) was heated at 80° C. for 6 hours. The reaction mixture was cool down to room temperature. quenched with water and then extracted with ethyl acetate. The organic extract was dried ($MgSO_4$) and evaporated under vacuum. After purification by Flash Chromatography on silica gel using as eluent methylene chloride/methanol/ammonia (95/5/0,5), the desired compound was obtained as an oil. A solution of this oil in methanol was saturated with gaseous hydrogen chloride. A solid was precipitated. The title compound hydrochloride was collected by filtration, washed with hexane and dried under vacuum (0.66 g).

Mp 65°–70° C.

| | Analysis $C_{25}H_{29}FN_2O \cdot HCl$ | | |
|---|---|---|---|
| | C | H | N |
| Found % | 68.43 | 7.21 | 6.39 |
| Calc. % | 70.00 | 7.05 | 6.53 |

$^1$H NMR (DMSO+$CDCl_3$) δ=12.42 (b, 1H), 8.28 (b, 1H), 7.3–6.8 (8H), 5.87 (b, 1H), 3.82 (s, 3H), 3.7–2.3 (12H), 1.8–1.2 (4H); MS (C.I.): [M+H]$^+$ 393 m/z

Following the above described process and using the appropriate halide synthesized according to Description 5, the following compound was prepared 5-methoxy-3-[N-(3-(4-fluoro-phenyl)-propyl)-1,2,5,6-tetrahydro-pyridin-3-ylmethyl]-1H-indole (Compound 15)

Mp 114°–116° C.

| | Analysis $C_{24}H_{27}N_2OF$ | | |
|---|---|---|---|
| | C | H | N |
| Found % | 76.16 | 7.20 | 7.40 |
| Calc. % | 76.16 | 7.19 | 7.40 |

$^1$H NMR ($CDCl_3$) δ=8.23 (b, 1H), 7.22 (d, 1H), 7.2–6.9 (6H), 6.84 (m, 1H), 5.56 (b, 1H), 3.84 (s, 3H), 3.37 (s, 2H), 2.90 (b, 2H), 2.55 (t, 2H), 2.52 (t, 2H), 2.39 (m, 2H), 2.18 (b, 2H), 1.79 (m, 2H); MS (C.I.): [M+H]$^+$ 379 m/z

Description 10

N-(2-bromo-ethyl)-4-fluoro-benzamide 4-fluoro-benzoyl chloride (3 ml; 0.026 mol) was added dropwise to a cold (~0° C.). Stirring mixture of 2-bromo-ethyl-amine hydrobromide (5 g; 0.0236 mol) and 10% aqueous sodium hydroxide (21 ml; 0.052 mol). Crystalline product started to precipitate out of the reaction mixture almost immediately. After 15 minutes of stirring, the product was collected by filtration, triturated with diethyl ether and dried under vacuum giving the desired compound as a white solid (4 g).

Following the above described process and using the appropriate acyl halide the following compounds can be prepared:

N-(2-bromo-ethyl)-2-thiophene-carboxamide
N-(2-bromo-ethyl)-1-adamantane-carboxamide All the above mentioned compounds were used as such without further purification.

EXAMPLE 6

5-methoxy-3-[N-(2-(4-fluoro-benzamide)-ethyl-1,2,5,6-tetrahydro-pyridin-3-ylmethyl]-1H-indole (Compound 16)

A mixture of compound of Description 5 [5-methoxy-3-(1,2,5,6-tetrahydro-pyridin-3-ylmethyl)-1H-indole] (1.5 g; 0.0062 mol) and compound of Description 10 [N-(2-bromoethyl)-4-fluoro-benzamide (1.68 g; 0.0068 mol) in dry acetonitrile. The reaction mixture was refluxed for 8 hours. The reaction was then concentrated under vacuum. Purification by Flash Chromatography of the crude product using silica gel and elution with methylene chloride/methanol/ammonia (95/5/0,5) yielded the desired compound. A solution of the desired compound in ethanol was saturated with gaseous hydrogen chloride. A solid was precipitated. The title compound hydrochloride was collected by filtration, washed with diethyl ether and dried under vacuum (0.3 g).

| | Analysis $C_{24}H_{26}N_3O_2F.HCl$ | | |
|---|---|---|---|
| | C | H | N |
| Found % | 63.87 | 6.27 | 9.13 |
| Calc. % | 64.93 | 6.13 | 9.47 |

$^1$H NMR (CDCl$_3$) δ=11.91 (b, 1H), 8.79 (b, 1H), 8.05 (m, 3H), 7.4–6.7 (6H), 5.87 (b, 1H), 4.4–3.1 (10H), 3.83 (s, 3H), 2.55 (m, 2H); MS (C.I.): [M+H]$^+$ 408 m/z

Following the above described process and using the appropriate 2-halo-ethyl-amide, the following compounds were prepared:

5-methoxy-3-[N-(2-(2-thiophene-carboxamide)-ethyl)-1,2,5,6-tetrahydro-pyridin-3-ylmethyl]-1H-indole (Compound 17)

Mp 185°–190° C.

| | Analysis $C_{22}H_{25}N_3O_2S.HCl$ | | |
|---|---|---|---|
| | C | H | N |
| Found % | 59.94 | 6.18 | 9.46 |
| Calc. % | 61.17 | 6.07 | 9.79 |

$^1$H NMR (DMSO) δ=10.78 (b, 1H), 10.27 (b, 1H), 8.96 (t, 1H), 7.9–7.7 (2H), 7.23 (d, 1H), 7.3–7.1 (2H), 6.98 (d, 1H), 6.71 (m, 1H), 5.73 (b, 1H), 3.74 (s, 3H), 4.0–3.0 (10H), 2.33 (m, 2H); MS (C.I.): [M+H]$^+$ 396 m/z 5-methoxy-3-[N-(2-(1-adamantane-carboxamide)-ethyl)-1,2,5,6-tetrahydro-pyridin-3-ylmethyl]-1H-indole (Compound 18)

Mp 128° C.

| | Analysis $C_{28}H_{37}N_3O_2$ | | |
|---|---|---|---|
| | C | H | N |
| Found % | 75.18 | 8.30 | 9.40 |
| Calc. % | 75.13 | 8.33 | 9.39 |

$^1$H NMR (CDCl$_3$) δ=7.99 (b, 1H), 7.24 (d, 1H), 7.03 (d, 1H), 6.97 (d, 1H), 6.84 (m, 1H), 6.25 (b, 1H), 5.62 (b, 1H), 3.85 (s, 3H), 3.39 (s, 2H), 3.30 (m, 2H), 2.85 (m, 2H), 2.54 (t, 2H), 2.51 (t, 2H), 2.17 (b, 2H), 2.01 (b, 3H), 1.9–1.6 (12H);

MS (C.I.): [M+H]$^+$ 448 m/z

EXAMPLE 7

5-Methoxy-3-(N-methyl-1,2,5,6-tetrahydro-pyridin-3-yl-5 methyl)-1-pentyl-indole (Compound 19)

To a suspension of sodium hydride (80% dispersion in mineral oil; 0.22 g; 0.0072 mol) in dry dimethylformamide (30 ml), compound 1 of Example 1 (5-Methoxy-3-(N-methyl-1,2,5,6-tetrahydro-pyridin-3-ylmethyl)-1H-indole) (1.54 g; 0.006 mol) was added portionwise at room temperature. After 30 minutes, a solution of 1-bromopentane (0.820 ml; 0.0066 mol) in dry dimethylformamide (5 ml) was added. The resultant mixture was stirred under nitrogen for 8 hours at room temperature. The reation mixture was quenched with a saturated solution of aqueous sodium carbonate and extracted with ethyl acetate. The organic extract was dried (MgSO$_4$) and evaporated under vacuum. After purification by Flash Chromatography on silica gel using as eluent methylene chloride/methanol/ammonia (95/5/0.5), the desired compound was obtained (0.77 g). A solution of the compound in ethanol was saturated with gaseous hydrogen chloride. A white solid was precipitated. The title compound hydrochloride was collected by filtration, washed with ethanol and dried under vacuum (0.84 g).

Mp 135° C.

| | Analysis $C_{21}H_{30}N_2O.HCl$ | | |
|---|---|---|---|
| | C | H | N |
| Found % | 67.79 | 8.77 | 7.5 |
| Calc. % | 69.5 | 8.61 | 7.72 |

$^1$H NMR (CDCl$_3$) δ=12.7 (b, 1H), 7.3–6.8 (4H), 5.85 (b, 1H), 4.03 (t, 2H), 3.84 (s, 3H), 3.47 (b, 4H), 3.23 (m, 2H), 2.74 (b, 3H), 2.40 (b, 2H), 1.80 (m, 2H), 1.5–1 (4H), 0.87 (t, 3H); MS (C.I.): [M+H]$^+$ 327 m/z

Following the above described process and using the appropriate halide, the following compounds were prepared:

5-methoxy-3-(N-methyl-1,2,5,6-tetrahydro-pyridin-3-ylmethyl)-1-(cyclo-propyl-methyl)-indole
(Compound 20)
Mp 95°–98° C.

| Analysis $C_{20}H_{26}N_2O.C_4H_6O_6$ | | | |
|---|---|---|---|
| | C | H | N |
| Found % | 62.68 | 7.03 | 6.15 |
| Calc. % | 62.59 | 7.0 | 6.08 |

$^1$H NMR (DMSO+CDCl$_3$) δ=7.31 (d, 1H), 7.15 (s, 1H), 6.95 (d, 1H), 6.75 (m, 1H), 5.66 (b, 5H), 4.11 (s, 2H), 3.94 (d, 2H), 3.75 (s, 3H), 3.35 (b, 2H), 3.23 (b, 2H), 2.82 (m, 2H), 2.53 (s, 3H), 2.25 (b, 2H), 1.18 (m, 1H), 0.6–0.2 (4H); MS (C.I.): [M+H]$^+$ 285 m/z 5-methoxy-3-[N-methyl-1,2,5,6-tetrahydro-pyridin-3-ylmethyl]-1-methyl-indole
(Compound 21)
Mp 126° C.

| Analysis $C_{17}H_{22}N_2O.HCl$ | | | |
|---|---|---|---|
| | C | H | N |
| Found % | 65.65 | 7.42 | 9.08 |
| Calc. % | 66.55 | 7.56 | 9.13 |

$^1$H NMR (CDCl$_3$) δ=12.6 (b, 1H), 7.3–6.7 (4H), 5.87 (b, 1H), 3.84 (s, 3H), 3.73 (s, 3H), 4.0–2.7 (11H). MS (C.I.): [M+H]$^+$ 271 m/z

EXAMPLE 8

5-Methoxy-3-[N-[4-(4-fluoro-phenyl)-4-(hydroxy-imino)-butyl]-1,2,5,6-tetrahydro-pyridin-3ylmethyl]-1H-indole
(Compound 22)

A mixture of Compound 8 of Example 2 (5-methoxy-3-[N-(4-(4-fluoro-phenyl)-4-oxo-butyl]-1,2,5,6-tetrahydro-pyridin-3-ylmethyl]-1H-indole) (0.9 g; 0.0022 mol) and hydroxylamine hydrochloride (0.61 g; 0.0044 mo) in methanol (70 ml) was refluxed for 4 hours. The solvent (methanol) was concentrated under vacuum. The residue was taken up with 30% aqueous ammonia and then extracted with ethyl acetate. The organic extract was dried (MgSO$_4$) and evaporated under vacuum. Purification by Flash Chromatography of the crude product using silica gel and elution with methylene chloride/methanol (93/7) yielded the desired compound as a light yellow solid (0.6 g).
Mp 129°–130° C.

| Analysis $C_{25}H_{28}N_3FO_2$ | | | |
|---|---|---|---|
| | C | H | N |
| Found % | 70.35 | 6.73 | 9.81 |
| Calc. % | 71.24 | 6.70 | 9.97 |

$^1$H NMR (DMSO) δ=11.17 (s, 1H), 10.64 (s, 1H), 7.65 (m, 2H), 7.19 (m, 2H), 7.13 (d, 1H), 7.05 (d, 1H), 6.95 (d, 1H), 6.70 (m, 1H), 5.51 (b, 1H), 3.72 (s, 3H), 3.29 (s, 2H), 2.76 (s, 2H), 2.68 (t, 2H), 2.37 (t, 2H), 2.31 (t, 2H), 2.05 (b, 2H), 1.57 (m, 2H); MS (C.I.): [M+H]$^+$ 422 m/z

Following the above described process and using the appropriate hydroxylamine derivative, the following compounds were prepared:

5-Methoxy-3-[N-[4-(4-fluoro-phenyl)-4-(benzyl-oxyimino)-butyl]-1,2,5,6-tetrahydro-pyridin-3ylmethyl]-1H-indole
(Compound 23)
Mp 61°–63° C.

| Analysis $C_{32}H_{34}N_3FO_2.HCl$ | | | |
|---|---|---|---|
| | C | H | N |
| Found % | 68.85 | 6.71 | 6.11 |
| Calc. % | 70.12 | 6.44 | 6.47 |

$^1$H NMR (CDCl$_3$) δ=12.19 (b, 1H), 8.41 (b, 1H), 7.56 (m, 2H), 7.4–6.8 (11H), 5.75 (b, 1H), 3.83 (s, 3H), 3.8–1.2 (16H); MS (C.I.): [M+H]$^+$ 512 m/z

[E] 5-Methoxy-3-[N-[4-(4-fluoro-phenyl)-4-(methoxy-imino)-butyl]-1,2,5,6-tetrahydro-pyridin-3ylmethyl]-1H-indole
(Compound 24)
Mp 86°–90° C.

| Analysis $C_{26}H_{30}N_3FO_2.C_4H_6O_6$ | | | |
|---|---|---|---|
| | C | H | N |
| Found % | 59.21 | 6.41 | 6.90 |
| Calc. % | 61.53 | 6.20 | 7.18 |

$^1$H NMR (DMSO) δ=10.70 (s, 1H), 7.44 (m, 2H), 7.30–7.15 (3H), 7.09 (d, 1H), 6.95 (d, 1H), 6.70 (m, 1H), 5.62 (b, 1H), 4.13 (s, 2H), 3.73 (s, 3H), 3.71 (s, 3H), 3.5 (b, 4H), 3.33 (s, 2H), 3.13 (b, 2H), 2.8–2.4 (6H), 2.16 (b, 2H), 1.6 (m, 2H); MS (C.I.): [M+H]$^+$ 436m/z

[Z] 5-Methoxy-3-[N-[4-(4-fluoro-phenyl)-4-(methoxy-imino)-butyl]-1,2,5,6-tetrahydro-pyridin-3-ylmethyl]-1H-indole
(Compound 25)
Mp 176–181

| Analysis $C_{26}H_{30}N_3FO_2.C_4H_6O_6$ | | | |
|---|---|---|---|
| | C | H | N |
| Found % | 60.01 | 6.38 | 6.97 |
| Calc. % | 61.53 | 6.20 | 7.18 |

$^1$H NMR (CDCl$_3$) δ=8.31 (b, 1H), 7.57 (m, 2H), 7.21 (d, 1H), 7.1–6.9 (4H), 6.83 (m, 1H), 5.57 (b, 1H), 3.92 (s, 3H), 3.84 (s, 3H), 3.36 (s, 2H), 2.91 (b, 2H), 2.70 (t, 2H), 2.53 (t, 2H), 2.44 (t, 2H), 2.19 (b, 2H), 1.73 (m, 2H); MS (C.I.): [M+H]$^+$ 436 m/z

EXAMPLE 9

5-Methoxy-3-[N-(4-(4-fluoro-phenyl)-4-hydroxy-butyl)-1,2,5,6-tetrahydro-pyridin-3-ylmethyl]-1H-indole (Compound 26)

Sodium borohydride (0.2 g; 0,0053 mol) was added to a cool (~5° C.) stirring mixture of compound 8 of Example 2 (5-methoxy-3-[N-(4-(4-fluoro-phenyl)-4-oxobutyl]-1,2,5,6-tetrahydro-pyridin-3-ylmethyl]-1H-indole) (1.08 g; 0.0027 mol) in isopropanol (20 ml). The reaction mixture was stirred at 5° C. for 4 hours. The reaction was then quenched with a saturated solution of aqueous sodium carbonate and the solvent (isopropanol) was evaporated under vacuum. The product was extracted with diethyl ether from the residual alkaline aqueous solution. The organic extract was dried (MgSO$_4$) and evaporated under vacuum giving the desired compound (0.8 g). A solution of the desired compound in diethyl ether was saturated with gaseous hydrogen chloride. The obtained precipitate which consists of the title compound hydrochloride, was collected by filtration, washed with diethyl ether and dried under vacuum (0.75 g).

Mp 160°–170° C.

| Analysis $C_{25}H_{29}FN_2O_2.HCl$ | | | |
|---|---|---|---|
| | C | H | N |
| Found % | 65.28 | 6.92 | 5.6 |
| Calc. % | 67.48 | 6.8 | 6.3 |

$^1$H NMR (DMSO) δ=10.83 (s, 1H), 10.46 (b, 1H), 7.4–7.1 (6H), 6.97 (d, 1H) 6.72 (m, 1H), 5.73 (b, 1H), 4.52 (t, 1H), 3.75 (s, 3H), 3.8–3.3 (5H), 3.2–2.9 (3H), 2.53 (m, 1H), 2.23 (m, 1H), 1.9–1.5 (2H), 1.55 (m, 2H); MS (C.I.): [M+H]$^+$ 409 m/z

Following the above described process the following compound was prepared:

5-methoxy-3-[N-(3-(4-fluoro-phenyl)-3-hydroxy-propyl)-1,2,5,6-tetrahydro-pyridin-3-ylmethyl]-1H-indole (Compound 27)

Mp 70° C.

| Analysis $C_{24}H_{27}N_2OF.HCl.H_2O$ | | | |
|---|---|---|---|
| | C | H | N |
| Found % | 64.34 | 6.84 | 6.10 |
| Calc. % | 64.21 | 6.74 | 6.24 |

$^1$H NMR (DMSO) δ=10.81 (s, 1H), 10.59 (b, 1H), 7.4–7.1 (6H), 6.97 (d, 1H), 6.71 (m, 1H), 5.71 (b, 1H), 4.62 (m, 1H), 3.74 (s, 3H), 3.9–3.7 (1H), 3.6–2.9 (7H), 2.51–2.25 (m, 2H), 1.98 (m, 2H); MS (C.I.): [M+H]$^+$ 395 m/z

Description 11
3-(2-chloro-ethyl)-benzofurane
i) 4-chloro-butyraldehyde-O-phenyl-oxime A mixture of 2-(3-chloro-propyl)-[1,3]-dioxolane (5.7 g; 0.038 mol), THF (50 ml) and aqueous acid chloride (1/1) was stirred at room temperature for 24 hours. O-phenyl-hydroxylamine hydrochloride (5 g; 0.034 mol) was then added and the resulting mixture was stirred at room temperature for 48 hours. The reaction mixture was concentrated under vacuum. Then the product was extracted with methylene chloride. The organic extract was dried (Mg SO$_4$) and evaporated under vacuum. After purification by Flash Chromatography on silica gel using as eluent hexane/ethyl acetate (95/5), the desired compound was obtained.

ii) 3-(2-chloroethyl)-benzofurane

A mixture of 4-chloro-butyraldehyde-O-phenyl-oxime (2.5 g; 0.0126 mol), acetic acid (50 ml) and boron trifluoride etherate (1.45 ml; 0.0115 mol) was heated at 100° C. for 1.5 hour. The reaction was then quenched with water and the product was extracted with diethyl ether. The organic extract was dried (Mg SO$_4$) and evaporated under vacuum.

After purification by Flash Chromatography on silica gel using as eluent methylene chloride, the desired compound was obtained

EXAMPLE 10

5-methoxy-3-[N-(2-benzofuran-3-yl)-ethyl)-1,2,5,6-tetrahydro-pyridin-3-ylmethyl]-1H-indole (Compound 28)

The title compound was prepared according to the procedure described in Example 5, using compound of Description 5 [5-methoxy-3-(1,2,5,6-tetrahydro-pyridin-3-ylmethyl)-1H-indole]and compound of Description 11 [3-(2-chloro-ethyl)-benzofurane]

Mp 96°–99° C.

| Analysis $C_{25}H_{26}N_2O_2.HCl$ | | | |
|---|---|---|---|
| | C | H | N |
| Found % | 69.4 | 6.70 | 6.33 |
| Calc. % | 70.99 | 6.43 | 6.62 |

$^1$H NMR (CDCl$_3$) δ=12.63 (b, 1H), 8.54 (s, 1H), 7.6–6.8 (9H), 5.87 (b, 1H), 3.3–2.1 (15H); MS (C.I.): [M+H]$^+$ 387 m/z

Description 12
3-trifluoromethyl-N-(2-chloroethylcarbonyl)-aniline

The title compound was prepared according to the known Schotten-Baumann procedure using 3-(trifluoromethyl)-aniline and 3-chloro-propionyl chloride.

The above mentioned compound was used as such without further purification.

EXAMPLE 11

5-methoxy-3-[N-(3-(3'-trifluoromethyl-phenyl-amino)-3-oxo-propyl)-1,2,5,6-tetrahydro-pyridin-3-ylmethyl]-1H-indole (Compound 29)

The title compound was prepared according to the procedure described in Example 5, using compound of Description 5 [5-methoxy-3-(1,2,5,6-tetrahydro-pyridin-3-ylmethyl)-1H-indole] and compound of Description 12 [3-trifluoromethyl-N-(2-chloroethyl-carbonyl)-aniline]

Mp 172° C.

| Analysis $C_{25}H_{26}N_3O_2F_3.HCl$ | | | |
|---|---|---|---|
| | C | H | N |
| Found % | 59.9 | 5.56 | 8.50 |
| Calc. % | 60.59 | 5.51 | 8.51 |

$^1$H NMR (CDCl$_3$) δ=11.39 (b, 1H), 10.28 (s, 1H), 8.27 (s, 1H), 8.08 (s, 1H), 7.76 (m, 1H), 7.4–7.2 (m, 3H), 7.01 (s,

1H), 6.91 (d, 1H), 6.81 (m, 1H), 5.81 (b, 1H), 3.81 (s, 3H), 3.9–3.8 (1H), 3.5–2.9 (9H), 2.77–2.31 (m, 2H); MS (C.I.): [M+H]$^+$ 458 m/z

EXAMPLE 12

5-methoxy-3-[N-(3-(3'-trifluoromethyl-phenyl-amino)-propyl)-1,2,5,6-tetrahydro-pyridin-3-ylmethyl]-1H-indole (Compound 30)

To a stirred solution of Compound 29 of Example 11 [5-methoxy-3-[N(3-(3'-trifluoromethyl-phenyl-amino)-3-oxo-propyl)-1,2,5,6-tetrahydro-pyridin-3-ylmethyl]-1H-indole] (1.7 g; 0.0037 mol) in anhydrous tetrahydrofuran (50 ml) at room temperature under nitrogen was carefully added lithium aluminium hydride (0.3 g; 0.0078 ml) and the resulting mixture was refluxed for 16 hours. The reaction was then quenched with successive additions of water, aqueous sodium hydroxide and then additional water and the resulting mixture filtered through diatomaceous earth [Celite®].

The solids were then washed with ethyl acetate. The combined filtrate was then washed with water, dried (Mg SO$_4$), and evaporated under vacuum.

After purification by Flash Chromatography on silica gel using as eluent methylene chloride/methanol/ammonia (95/5/0.5), the desired compound was obtained. A solution of the compound in ethanol was saturated with gaseous hydrogen chloride. A solid was precipitated. The title compound hydrochloride was collected by filtration, washed with hexane and dried under vacuum Mp 132° C.

| | Analysis $C_{25}H_{28}N_3OF_3.HCl$ | | |
|---|---|---|---|
| | C | H | N |
| Found % | 62.26 | 6.07 | 8.70 |
| Calc. % | 62.56 | 6.09 | 8.75 |

$^1$H NMR (DMSO) δ=10.71 (b, 1H), 10.5 (b, 1H), 7.4–6.6 (8H), 5.77 (b, 1H), 3.75 (s, 3H), 3.9–1.9 (14H); MS (C.I.): [M+H]$^+$ 444 m/z

Description 13

5-methoxy-3-[N-(4-(4-fluoro-phenyl)-4-amino-butyl)]-1,2,5,6-tetrahydro-pyridin-3-ylmethyl]-1H-indole To a stirred solution of Compound 22 of Example 8 [5-methoxy-3-[N-[4-(4-fluoro-phenyl)-4-(hydroxy-imino)-butyl]-1,2,5,6-tetrahydro-pyridin-3-ylmethyl]-1H-in-dole] (1 g; 0.0023 mol) in anhydrous tetrahydro furan (80 ml) at room temperature under nitrogen was carefully added lithium aluminium hydride (0.45 g; 0.0118 mol) and the resulting mixture was heated at reflux for 8 hours. The reaction was then quenched with successive additions of water, aqueous sodium hydroxide and then additional water and the resulting mixture filtered through diatomaceous earth (Celite$^{(R)}$). The solids were then washed with ethyl acetate. The combined filtrate was then washed with water, dried (Mg SO$_4$), and evaporated under vacuum. After purification by Flash Chromatography on silica gel using as eluent methylene chloride/methanol/ammonia (92/8/0.8), the desired compound was obtained (0.330 g)

EXAMPLE 13

5-methoxy-3-[N-(4-fluoro-phenyl)-4-(acetyl-amino) butyl]-1,2,5,6-tetrahydro-pyridin-3-ylmethyl]-1H-indole (Compound 31)

A mixture of compound of Description 13 [5-methoxy-3-[N-(4-(4-fluoro-phenyl)-4-amino-butyl)]-1,2,5,6-tetrahydro-pyridin-3-ylmethyl]-1H-indole] (0.330 g; 0.00081 mol) in methylene chloride (40 ml) and acetic anhydride (3 ml) was stirred at room temperature for 4 hours. The reaction mixture was quenched with aqueous sodium bicarbonate and the product was extracted with methylene chloride. The organic extract was dried (Mg SO$_4$) and evaporated under vacuum. After purification by Flash Chromatography on silica gel using as eluent methylene chloride/methanol/ammonia (94/6/0.6). A solution of the compound in ethanol was treated with the stechiometric amount of oxalic acid in ethanol. A solid was precipitated. The title compound oxalate was collected by filtration, washed with ethyl acetate and dried under vacuum Mp 92° C.

| | Analysis $C_{27}H_{32}N_3O_2F.C_2H_2O_4$ | | |
|---|---|---|---|
| | C | H | N |
| Found % | 63.2 | 6.70 | 7.2 |
| Calc. % | 64.55 | 6.35 | 7.79 |

$^1$H NMR (DMSO) δ=10.81 (s, 1H), 8.35 (d, 1H), 7.4–7.1 (6H), 6.96 (d, 1H), 6.71 (m, 1H), 5.71 (b, 1H), 4.75 (m, 1H), 3.74 (s, 3H), 3.52 (b, 2H), 3.39 (s, 2H), 3.14 (b, 2H), 3.00 (b, 2H), 2.30 (b, 2H), 1.83 (s, 3H), 1.8–1.4 (4H); MS (C.I.): [M+H]$^+$ 450 m/z

EXAMPLE 14

5-methoxy-3-[N-(4-(2-thienyl)-4-oxo-butyl)-1,2,5,6-tetrahydro-pyridin-3-ylmethyl]-1H-indole (Compound 32)

The title compound was prepared according to the procedure described in Example 5, using compound of Description 5 [5-methoxy-3-(1,2,5,6-tetrahydro-pyridin-3-ylmethyl)-1H-indole) and the commercial halide 4-chloro-2'-butyrothienone Mp 140°–150° C.

| | Analysis $C_{23}H_{26}N_2O_2S.HCl$ | | |
|---|---|---|---|
| | C | H | N |
| Found % | 63.9 | 6.1 | 6.0 |
| Calc. % | 64.1 | 6.31 | 6.5 |

$^1$H NMR (DMSO) δ=10.79 (s, 1H), 10.28 (b, 1H), 8.02 (m, 1H), 7.93 (m, 1H) 7.3–7.1 (3H), 6.98 (d, 1H), 6.71 (m, 1H), 5.75 (b, 1H), 3.78 (gem, 1H), 3.75 (s, 3H), 3.6–2.9 (9H), 2.6–2.2 (2H), 1.99 (m, 2H); MS (C.I.): [M+H]$^+$ 395 m/z Following the above mentioned procedure and using the appropriate commercial halide, the following compounds were prepared:

5-methoxy-3-[N-(4-(4-methoxy-phenyl)-4-oxo-butyl)-1,2,5,6-tetrahydro-pyridin-3-ylmethyl]-1H-indole (Compound 33)
Mp 140°–147° C.

Analysis
C$_{20}$H$_{26}$N$_2$O$_2$.HCl

| | C | H | N |
|---|---|---|---|
| Found % | 68.4 | 6.45 | 6.0 |
| Calc. % | 68.63 | 6.87 | 6.16 |

$^1$H NMR (DMSO) δ=10.79 (b, 1H), 8.36 (b, 1H), 7.83 (d, 2H), 7.26 (d, 1H) 7.10 (d, 1H), 6.92 (d, 2H), 7.0–6.9 (1H), 6.82 (m, 1H), 5.86 (b, 1H), 3.87 (s, 3H), 3.9–3.7 (1H), 3.6–2.5 (10H), 2.38 (m, 1H), 2.17 (m, 2H); MS (C.I.): [M+H]$^+$ 419 m/z 5-methoxy-3-[N-(3-ethyl-3-oxo-propyl)-1,2,5,6-tetrahydro-pyridin-3-ylmethyl]-1H-indole (Compound 34)
Mp 156°–160° C.

C$_{20}$H$_{26}$N$_2$O$_2$.HCl

| | C | H | N |
|---|---|---|---|
| Found % | 66.03 | 7.2 | 7.1 |
| Calc. % | 66.19 | 7.5 | 7.72 |

$^1$H NMR (DMSO) δ=10.80 (s, 1H), 10.49 (b, 1H), 7.21 (d, 1H), 7.17 (d, 1H) 6.97 (d, 1H), 6.72 (m, 1H), 5.72 (b, 1H), 3.75 (s, 3H), 3.70 (gem, 1H), 3.6–3.2 (6H), 3.1–2.9 (3H), 2.45 (q, 2H), 2.26–2.2 (2H), 0.92 (t, 3H); MS (C.I.): [M+H]$^+$ 327 m/z 5-methoxy-3-[N-(4-(4-methyl-phenyl)-4-oxo-butyl)-1,2,5,6-tetrahydro-pyridin-3-ylmethyl-1H-indole (Compound 35)
Mp 86°–93° C.

Analysis
C$_{26}$H$_{30}$N$_2$O$_2$.HCl

| | C | H | N |
|---|---|---|---|
| Found % | 71.0 | 6.9 | 6.1 |
| Calc. % | 71.14 | 7.12 | 6.38 |

$^1$H NMR (CDCl$_3$) δ=12.22 (b, 1H), 8.35 (s, 1H), 7.80 (d, 2H), 7.3–7.2 (3H) 7.11 (s, 1H), 6.93 (d, 1H) 6.82 (m, 1H), 5.87 (b, 1H), 3.86 (gem, 1H), 3.82 (s, 3H) 3.8–2.7 (1OH), 2.41 (s, 3H), 2.5–2.2 (1H), 2.18 (m, 2H); MS (C.I.): [M+H]$^+$ 403 m/z

EXAMPLE 15

5-methoxy-3-[N-methyl-1,2,5,6-tetrahydro-pyridin-3-yl-methyl]-1-(4-fluoro-phenyl)-indole (Compound 36)

A mixture of compound 1 of Example 1 [5-methoxy-3-(N-methyl-1,2,5,6-tetrahydro-pyridin-3-yl-methyl)-1H-indole] (1 g; 0.0039 mol), 1-fluoro-4-iodobenzene (0.6 ml; 0.0058 mol), finally powdered anhydrous K$_2$CO$_3$ (0.7 g; 0.0051 mol), copper bromide (0.3 g; 0.0023 mol) and copper bronze (0.002 g) in 1-methyl-2-pyrrolidone (20 ml) was heated at 180° C. under nitrogen for 4 hours. After cooling (below 100° C.) the mixture was poured into diluted hydrochloric acid. After the mixture was stirred, the precipitated material was filtered off, washed with water, and subsequently dried in vacuo.

Purification was performed by dissolving in methylene chloride, treating the solution with activated carbon, and finally by Flash chromatography on silica gel using as eluent methylene chloride/methanol/ammonia (95/5/0.5). A solution of the desired compound in diethyl ether was saturated with gaseous hydrogen chloride. The title compound hydrochloride was collected by filtration, washed with diethyl ether and dried under vacuum Mp 200° C.

Analysis
C$_{22}$H$_{23}$N$_2$OF$_3$.HCl

| | C | H | N |
|---|---|---|---|
| Found % | 67.9 | 6.2 | 7.01 |
| Calc. % | 68.3 | 6.5 | 7.24 |

$^1$H NMR (DMSO) δ=10.43 (b, 1H), 7.7–7.3 (6H), 7.11 (d, 1H), 6.84 (m, 1H), 5.85 (b, 1H), 3.80 (s, 3H), 3.75 (gem, 1H), 3.6–3.4 (4H), 3.05 (m, 1H), 2.78 (d, 3H), 2.50 (m, 1H), 2.30 (m, 1H); MS (C.I.): [M+H]$^+$ 351 m/z

EXAMPLE 16

5-methoxy-3-(N-methyl-piperidin-3-ylmethyl)-1H-indole (Compound 37)

To a stirred solution of compound of Description 6 [5-methoxy-3-(piperidin-3-ylmethyl)-1H-indole] (2 g, 0.0082 mol) in methanol (50 ml) was added dropwise aqueous formaldehyde (40%) (5.63 ml; 0.082 mol). The mixture was heated at reflux for 2 hours. The reaction mixture was cooled at 10° C. and then sodium borohydride (0.93 g; 0.025 mol) was added. The resulting mixture was stirred at room temperature for 1.5 hours. The reaction was then quenched with water and the solvent (methanol) was evaporated under vacuum. The product was extracted with ethyl acetate, the organic extract was dried (Mg SO$_4$) and evaporated under vacuum, then the compound was triturated with diethyl ether and dried under vacuum giving the title compound as a solid (1.8 g)

Mp 112°–114° C.

Analysis
C$_{16}$H$_{22}$N$_2$O

| | C | H | N |
|---|---|---|---|
| Found % | 74.3 | 8.84 | 10.73 |
| Calc. % | 74.38 | 8.58 | 10.84 |

$^1$H NMR (CDCl$_3$) δ=8.15 (b, 1H), 7.3–6.7 (4H), 3.85 (s, 3H), 2.80 (m, 2H), 2.61 (d, 2H), 2.23 (s, 3H), 2.4–0.7 (7H); MS (C.I.): [M+H]$^+$ 259 m/z

EXAMPLE 17

5-methoxy-3-[N-(α-tetralon-2-ylmethyl)-1,2,5,6-tetrahydro-pyridin-3-ylmethyl]-1H-indole (Compound 38)

The title compound was prepared according to a known Mannich procedure, using compound of Description 5

[5-methoxy-3-(1,2,5,6-tetrahydro-pyridin-3-ylmethyl)-1H-indole] and the commercial compound α-tetralone
Mp 154°–156° C.

| Analysis $C_{26}H_{28}N_2O_2.HCl$ | | | |
|---|---|---|---|
| | C | H | N |
| Found % | 70.89 | 6.71 | 6.32 |
| Calc. % | 71.46 | 6.69 | 6.41 |

$^1$H NMR (DMSO) δ=10.80 (s, 1H), 10.26 (b, 1H), 7.88 (d, 1H), 7.57 (m, 1H), 7.4–7.3 (2H) 7.23 (m, 1H), 7.17 (s, 1H) 6.98 (d, 1H), 6.71 (d, 1H), 3.76 (m, 1H), 3.9–2.8 (11H), 3.76 (s, 3H), 2.6–2.2 (3H), 1.88 (m, 1H); MS (C.I.): [M+H]$^+$ 401 m/z

EXAMPLE 18

5-methoxy-3-[N-(4-(4-fluoro-phenyl)-4-oxo-butyl) piperidin-3-ylmethyl]-1-H-indole
(Compound 39)

A mixture of compound of Description 6 [5-methoxy-3-(piperidin-3-ylmethyl)-1H-indole] (2 g; 0.0082 mol), sodium bicarbonate (0.68 g; 0.0082 mol), KI (0.087 g; 0.00053 mol) and 2-(3-chloropropyl)-2-(4-fluorophenyl)-1, 3-dioxolane [2.2 g (1,8 ml); 0.009 mol] in dry dimethylformamide (25 ml) and tetrahydrofuran (25 ml), was heated under reflux for 5 hours. After evaporation under vacuum, the residue was flash chromatographed on silica gel using as eluent methylene chloride/methanol/ammonia (95/5/0.5) and the desired compound was obtained. A solution of the compound in ethanol was saturated with gaseous hydrogen chloride, a solid was precipitated. The title compound hydrochloride was collected by filtration.

The following not limitative examples of pharmaceutical compositions according to the invention are given:

EXAMPLE 19

| Tablets | |
|---|---|
| active ingredient | 10 mg |
| lactose | 187 mg |
| corn starch | 50 mg |
| magnesium stearate | 3 mg |

Method of preparation: the active ingredient, lactose and corn starch were mixed and homogeneously moistened with water. After screening of the moist mass and drying in a tray drier, the mixture was again passed through a screen and magnesium stearate was added. Then the mixture was pressed into tablets weighing 250 mg each. Each tablet contains 10 mg of active ingredient.

EXAMPLE 20

| Capsules | |
|---|---|
| active ingredient | 10 mg |
| lactose | 188 mg |
| magnesium stearate | 2 mg |

Method of preparation: the active ingredient was mixed with the auxiliary products, and the mixture was passed through a screen and mixed homogeneously in a suitable device. The resulting mixture was filled into hard gelatine capsules (200 mg per capsule); each capsule contains 10 mg of active ingredient.

EXAMPLE 21

| Ampoules | |
|---|---|
| active ingredient | 2 mg |
| sodium chloride | 9 mg |

Method of preparation: the active ingredient and sodium chloride were dissolved in an apropriate amount of water for injection. The resulting solution was filtered and filled into vials under sterile conditions.

EXAMPLE 22

| Suppositories | |
|---|---|
| active ingredient | 25 mg |
| semisynthetic glicerides | 1175 mg |

Method of preparation: the semisynthetic glicerides of fatty acids were melted and the active ingredient was added while stirring homogeneously. After cooling at a proper temperature the mass was poured into preformed moulds for suppositories weighing 1200 mg each. Each suppository contains 25 mg of active ingredient.

EXAMPLE 23

| Nasal spray | |
|---|---|
| active ingredient | 80 mg |
| benzalconchloride | 0,1 mg |
| sodium chloride | 8 mg |
| EDTA | 1 mg |
| sodium phosphate (buffer pH 6,5) | 10 mg |
| polysorbate 80 | 10 mg |
| bidistilled water q.s. to | 2 ml |

Method of preparation: the single components were added in the suitable volume of bidistilled water by stirring until a complete dissolution before an further addition. After taking to volume, the solution was filtered upon sterilising filter, introduced in suitable bottles and blocked up by the opportune dosage system.

We claim:
1. A compound of general formula (I)

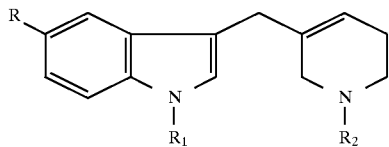

wherein:
R represents H, $C_{1-6}$ alkyl, $C_{1-3}$ alkoxy, benzyloxy, halogen, hydroxy, cyano or $C_{1-6}$ acyl;
$R_1$ represents H, $C_{1-6}$ alkyl, phenyl, fluorophenyl, $C_{3-6}$ cycloalkyl $C_{1-2}$ alkyl or $C_{1-3}$ alkyl bearing a phenyl or fluorophenyl group;
$R_2$ represents H, $C_{1-6}$ alkyl, $C_{1-3}$ alkyl bearing a phenyl, phenoxy, or anilino, each group being optionally substituted by one or more substituents selected from $C_{1-3}$ alkyl, $C_{1-3}$ alkoxy, amino, halogen or trifluoromethyl; or $R_2$ is a group selected from

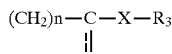 (a)

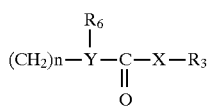 (b)

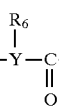

where n is an integer from 1 to 3;
$R_3$ represents a phenyl or thienyl group, each group being optionally substituted by one or more substituents selected from $C_{1-3}$ alkyl, halogen or trifluoromethyl; $C_{1-6}$ alkyl or $C_4$–$C_{10}$ cycloalkyl;
M represents oxygen or nitrogen, or when the bond C—M is single represents NH;
Z is absent when M is oxygen or it represents H, $C_{1-6}$ acyl or $OR_4$ where $R_4$ is hydrogen, $C_{1-3}$ alkyl, $C_{1-3}$ alkyl bearing a phenyl being optionally substituted by one or more substituents selected from $C_{1-3}$ alkyl, $C_{1-3}$ alkoxy, halogen, trifluoromethyl;
X is absent or it represents $CH_2$ or $NR_5$ where $R_5$ is H or lower alkyl;
Y represents CH or nitrogen atom;
$R_6$ represents hydrogen, $C_{1-3}$ alkyl, phenyl or $R_3$ and $R_6$ together with the carbonyl group to which they are bound constitute benzocondensed cycloalkanones of formula

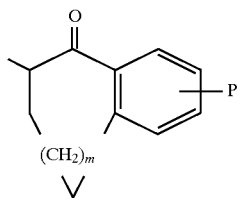 (c)

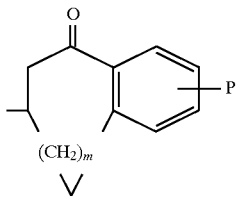 (d)

m is an integer form 0 to 2;
P represents H, $C_{1-3}$ alkyl, halogen or trifluoromethyl, with the following provisos:
when R is hydrogen and $R^2$ is methyl, $R^1$ is not phenyl and acid addition salts thereof.

2. A compound selected from:

5-methoxy-3-(N-methyl-1,2,5,6-tetrahydro-pyridin-3-ylmethyl)-1H-indole 5-methoxy-3-[N-(2-(4-amino-phenyl)-ethyl)-1,2,5,6-tetrahydro-pyridin-3-ylmethyl]-1H-indole)

5-methoxy-3-[N-(4'-fluoro-phenoxy-ethyl)-1,2,5,6-tetrahydro-pyridin-3-ylmethyl]-1H-indole 5-methoxy-3-[N-(4-(4-fluoro-phenyl)-4-oxo-butyl)-1,2,5,6-tetrahydro-pyridin-3-ylmethyl]-1H-indole 5-methoxy-3-[N-(3-(4-fluoro-phenyl)-3-oxo-propyl)-1,2,5,6-tetrahydro-pyridin-3-ylmethyl]-1H-indole 5-methoxy-3-[N-(4-(4-fluoro-phenyl)-butyl)-1,2,5,6-tetrahydro-pyridin-3-ylmethyl]-1H-indole 5-methoxy-3-[N-2(4-fluoro-benzamido)ethyl)-1,2,5,6-tetrahydro-pyridin-3-ylmethyl]-1H-indole 5-methoxy-3-[N-(3-(4-fluoro-phenyl)-propyl)-1,2,5,6-tetrahydro-pyridin-3-ylmethyl]-1H-indole 5-methoxy-3-[N-(4-(2-thienyl)-4-oxo-butyl)-1,2,5,6-tetrahydro-pyridin-3-ylmethyl]-1H-indole or acid addition salts thereof.

3. A physiologically acceptable acid addition salt of a compound of general formula (I) according to claim 1.

4. The physiologically acceptable acid addition salt according to claim 3, wherein the acid is hydrochloric, maleic or fumaric acid.

5. A pharmaceutical composition comprising as active ingredient an effective amount of a compound of general formula (I), as defined in claim 1, or a physiologically acceptable acid addition salt thereof, in association with pharmaceutically acceptable carriers, diluents or excipients.

* * * * *